United States Patent [19]

Erb

[11] E Re. 29,345

[45] Reissued Aug. 9, 1977

[54] METHOD AND APPARATUS FOR NON-SURGICAL, REVERSIBLE STERILIZATION OF FEMALES

[75] Inventor: Robert A. Erb, Valley Forge, Pa.

[73] Assignee: The Franklin Institute, Philadelphia, Pa.

[21] Appl. No.: 679,185

[22] Filed: Apr. 22, 1976

Related U.S. Patent Documents

Reissue of:

[64] Patent No.: 3,805,767
Issued: Apr. 23, 1974
Appl. No.: 335,816
Filed: Feb. 26, 1973

[51] Int. Cl.[2] ..... A61B 19/00

[52] U.S. Cl. ..... 128/1 R; 128/130; 128/303 R

[58] Field of Search ..... 128/1 R, 2 R, 130, 303 R, 128/234–236, 151, 152

[56] References Cited

U.S. PATENT DOCUMENTS

| | | | |
|---|---|---|---|
| 854,399 | 5/1907 | Bridge | 128/236 X |
| 3,042,021 | 7/1962 | Read | 128/130 X |
| 3,182,662 | 5/1965 | Shirodkar | 128/303 R |
| 3,422,813 | 1/1969 | Braley et al. | 128/1 R |
| 3,648,683 | 3/1972 | Brodie | 128/1 R |
| 3,680,542 | 8/1972 | Cimber | 128/1 R |
| 3,707,146 | 12/1972 | Cook et al. | 128/2 R |
| 3,918,443 | 11/1975 | Vennard et al. | 128/130 |

FOREIGN PATENT DOCUMENTS

| | | | |
|---|---|---|---|
| 819,629 | 7/1937 | France | 128/236 |

OTHER PUBLICATIONS

Stevenson et al., Jour. Obstet. & Gynec. of Gt. Brit., Nov. 1972, vol. 79, pp. 1028–1039.

Thompson et al., Human Sterilization – 1971 – Charles C. Thomas, Pub. Chapt. 30, pp. 353–359.

Rakshit – Human Sterilization – 1971, Charles C. Thomas – Pub. Chapt. 20, pp. 213–221.

*Primary Examiner*—Dalton L. Truluck

*Attorney, Agent, or Firm*—Dorfman, Herrell and Skillman

[57] ABSTRACT

A method and apparatus is provided for non-surgical reversible sterilization of females. In the method of this invention an apparatus to which a removable tip is attached is inserted into the uterus. The tip is aligned with the uterine end of the oviduct. A curable elastomeric composition is injected, through an aperture in the tip, into the oviduct in an amount sufficient to fill the portion of the oviduct adjacent to the uterus. The elastomeric composition is allowed to solidify and adhere to the above noted tip. The apparatus is then removed with the tip being ejected from the apparatus so as to remain adhered to the resulting oviduct block. The above procedure is repeated for the opposite oviduct. The resulting oviduct blocks prevent the passage of ovum from the ovaries to the uterus and sperm from entering the oviduct thereby preventing conception. The oviduct blocks if desired can be removed non-surgically by utilizing an apparatus which grips the tip portion of the oviduct block and extracts the entire oviduct block from the oviduct.

29 Claims, 5 Drawing Figures

METHOD AND APPARATUS FOR NON-SURGICAL, REVERSIBLE STERILIZATION OF FEMALES

Matter enclosed in heavy brackets [ ] appears in the original patent but forms no part of this reissue specification; matter printed in italics indicates the additions made by reissue.

The invention described herein was reduced to practice in the course of work under a grant or award from the Department of Health, Education and Welfare.

BACKGROUND OF THE INVENTION

1. Field of the Invention

This invention is concerned with a method and apparatus for non-surgical, reversible sterilization of females.

2. Description of the Prior Art

One of the more pressing problems which is encountered in the World today is that of over population. The problem of over population which has been a substantial problem for a considerable period of time in certain highly populated areas, such as Asia and the Indian Sub-Continent is now becoming a problem in less populated areas of the World such as Europe and the Americas. Over population results in such long range problems as pollution, famine and even war.

Birth control has been relied on as the principal means to control over population. In the field of birth control the prevention of conception is considerably more acceptable for controlling population growth than abortion. However, the methods heretofore suggested for contraception have had certain inherent problems which limited the applicability and effectiveness.

The ideal contraception method should be 100 percent effective in preventing conception; should not rely on willpower; should not interfere with the satisfaction of sexual relationships, and should be low in cost taking into consideration the effective life of the contraceptive method. In addition the contraceptive method must now have any harmful psychological side effects. An extremely important feature of an ideal contraceptive method especially for family planning is that it be reversible so that it will be possible to have additional children if desired.

The most common methods of contraception which are currently employed on a mass scale each have certan inherent deficiencies which limit their usefulness. The use of such techniques and devices such as rhythm, withdrawal, condoms and diaphragms and vaginal foams all have been found to be highly unreliable. The more recently promoted methods such as intrauterine devices and use of contraceptive pills likewise have certain defects which limit their effectiveness. The intrauterine devices cannot be utilized by all females and there is some indication that they cause irritation and discomfort and are often rejected by females. The contraceptive pill cannot be utilized by many females due to incompatability with their normal hormone balance. Furthermore, the use of the pill has been found to increase the risks of certain [carcigenic] *carcinogenic* conditions.

There are currently two methods in wide use which are generally considered to be effective contraceptive methods. These are oviduct ligation for females and vasectomy for males. In both these methods the ducts from the reproductive organs are severed and accordingly the contraceptive technique if properly performed and there is no natural regeneration are 100% effective. However, both methods have the defect that it is difficult, if not impossible, to reverse the procedure so as to restore the normal reproductive capacity.

It has been well established by gynecologists that a primary cause of infertility in females is blockage of the oviducts from the ovary to the uterus. The ovum when discharged from the ovaries is absorbed by the body and is prevented from coming in contact with the sperm and accordingly conception does *not* occur. Females having this natural condition normally do not even realize it exists and do not suffer any adverse side effect besides being infertile. Having been made aware of this natural condition those skilled in the art have suggested artificial blocking of the oviduct to impart sterility.

It was reported by Corfman et al. in [Obstetrices] *Obstetrics* and Gynecology Vol. 27 No. 6 pages 880–883 (June 1966) that various substances could be injected transcervically into the oviducts.

Hefnawi et al. Amr. J. Obst and Gynec, Vol. 99, No. 3 pages 421–427 (Oct. 1, 1967) reported attempts to block the oviducts by the injecting of medical grade elastomeric materials in the uncured state into the oviducts and allowing the material to solidify in the oviducts. The elastomeric material was thinned prior to injection so as to have a relatively fluid mixture for injection. The reported results obtained with rabbits was quite unsatisfactory. The incidence of pregnancy after insertion of the oviduct blocks was quite high. Effective sterilization was only achieved if the plug was placed in the medial portion of the oviduct. To remove the plug it was necessary to conduct laparotomy. A further problem which was reported was the tendency for the plug to migrate from the oviduct into either the uterine cavity or even more dangerously into the peritoneal cavity.

Rakshit reported in the Calcutta Med J 65, No. 3 (Mar., 1968) attempts to use various materials to block the oviducts to prevent conception. It was suggested to use a plastic material of a nature which solidifies after being mixed with a catalyst to form the oviduct blocks. Rakshit specifically taught however that because of high viscosity the silicone rubbers could not be injected transvaginally and laparotomies were conducted to inject the material directly into the uretus. The material was then allowed to flow into the oviducts. It was suggested in this article by Rakshit that it may be possible to introduce a plastic material transcervically into the uterus and then to allow it to flow in the oviducts. Using this method however the resulting oviduct blocks would have to be removed surgically to reestablish fertility.

Rakshit further reported in Human Sterilization edited by Ralph Rechart (1971) pages 213–221 the technique of attempting to form oviduct blocks by inserting a cannula directly into the uterus through the cervix and filling the uterus with a curable liquid silicone plastic. The injected silicone plastic was allowed to flow into the oviducts and cure in place to form the desired oviduct blocks. The excess material was then removed from the uterus. The reported results were not promising. On tests reported on 14 women there were nine satisfactory blockages, three doubtful cases and two negative cases. Further, in order to remove the oviduct blocks it was necessary to conduct a laparotomy.

SUMMARY OF THE INVENTION

In accordance with this invention a method and apparatus is provided to form oviduct blocks which prevent conception when in place and can be non-surgically removed if desires. The apparatus is inserted through the cervical os into the uterus. The tip of the apparatus is then aligned with the uterine end of the oviduct. A mixture of a fluid elastomeric material and a catalyst for polymerizing the elastomeric mixture is injected through an aperture in the tip into the oviduct. The elastomeric material is allowed to solidify and to adhere to the tip. The tip is released so that it remains with the injected elastomeric material to form the oviduct block of this invention. The apparatus is then removed. The oviduct block can be removed nonsurgically by inserting an instrument into the uterus through the cervix which grips the tip of the oviduct block and then withdrawing the oviduct block which restores normal fertility.

DETAILED DESCRIPTION OF THE PREFERRED EMBODIMENTS

Figure 2:
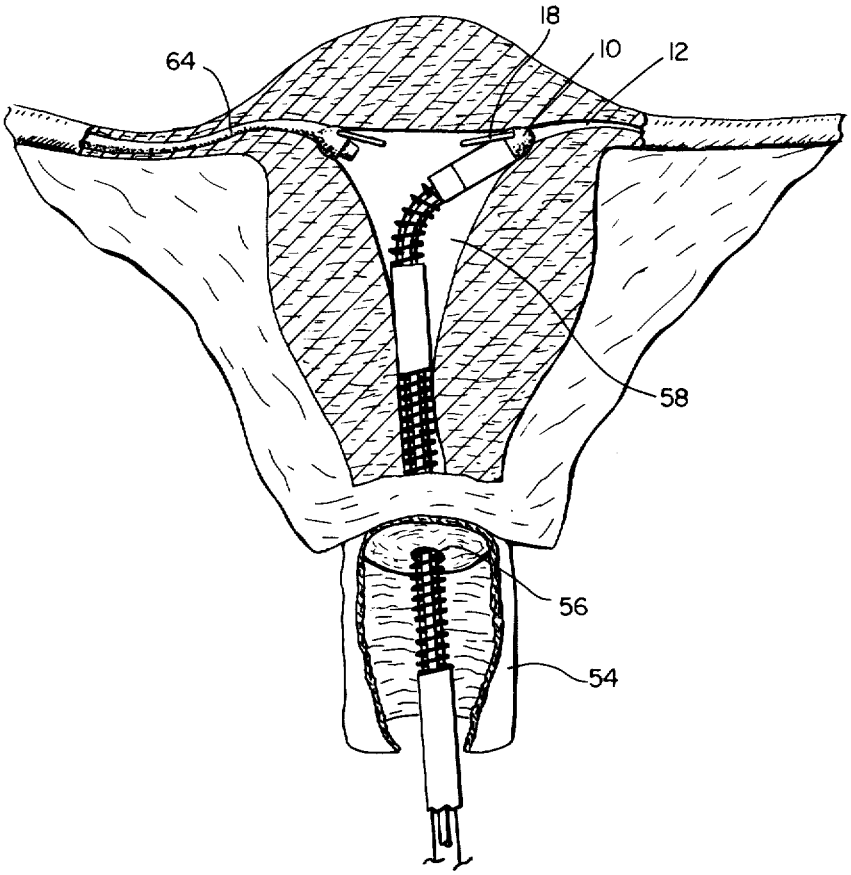
FIG. 2 is an illustration in partial cross-section of a uterus, the cervix and a portion of the vagina. The uterus is illustrated with an oviduct block insert in one of the oviduct and the terminal end of the apparatus of FIG. 1 positioned for insertion of an oviduct block into the opposite oviduct.

In the method of this invention an oviduct block is formed in situ in the oviduct. The oviduct block is most preferable formed from a medical inert plastic which has approximately the same modulus of elasticity as the oviduct. The selection of material having the proper modulus of elasticity appears to both prevent expulsion of the oviduct block and substantially eliminates any physical discomfort. The materials which have been found most useful in the method of this invention are the commercially available medical grade silicone elastomers. The uncured silicone elastomer in the fluid state is blended with a catalyst for solidifying the elastomer and a dilution fluid to control the viscosity during injection and also to control the modulus of elasticity of the cured solidified material. It is preferable to also include a radiopaque material in the mixture to facilitate the placement of the oviduct block and to facilitate removal of the oviduct block if [desires] *desired.*

A tip 10 is molded from an inert plastic material to which the injected elastomeric material will adhere on solidification. In this regard it should be noted that silicone-rubber is ideally suited for this purpose when a silicone elastomer is used for formation of the oviduct block.

As shown in the drawing the portion of the tip 10 which will be in contact with uterine end of the oviduct 12 has a spherical configuration. The tip 10 has an aperture 14 which extends throughout the entire length of the tip [14] *10.* In addition the tip as illustrated has a series of annular piston rings 16 molded into the interior [portion] surface of the aperture 14. The tip 10 further includes a loop 18 which is preferably a thread of a material which is inert in uterine fluids, such as nylon.

Figure 1:
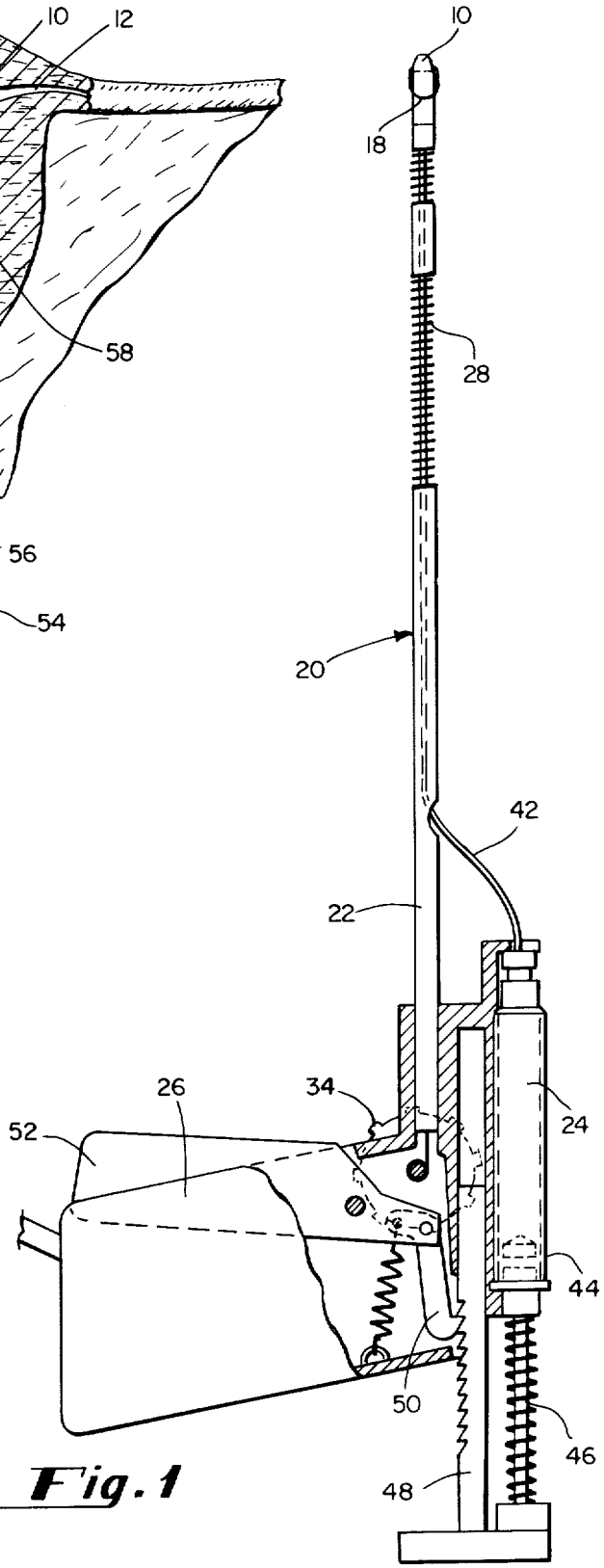
FIG. 1 is an illustration in partial cross-section of an apparatus especially adopted for use in the method of this invention.
Figure 3:
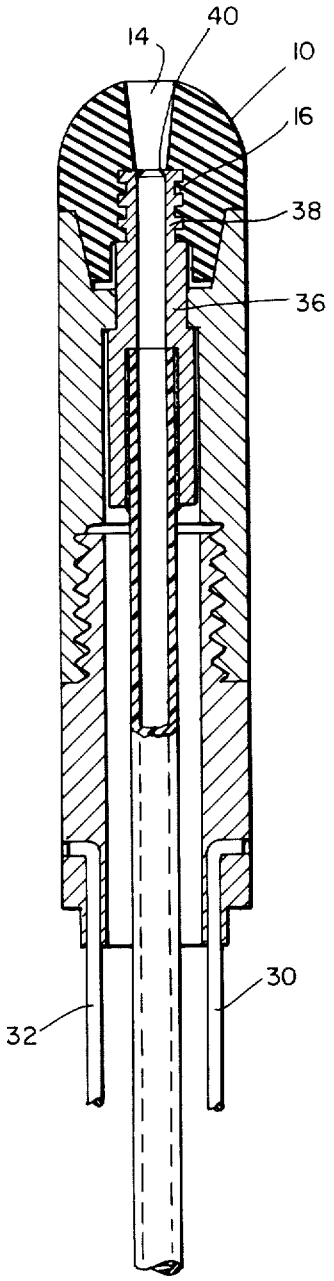
FIG. 3 is an enlarged illustration taken in partial cross-section of the terminal end of the apparatus of FIG. 1.
Figure 4:
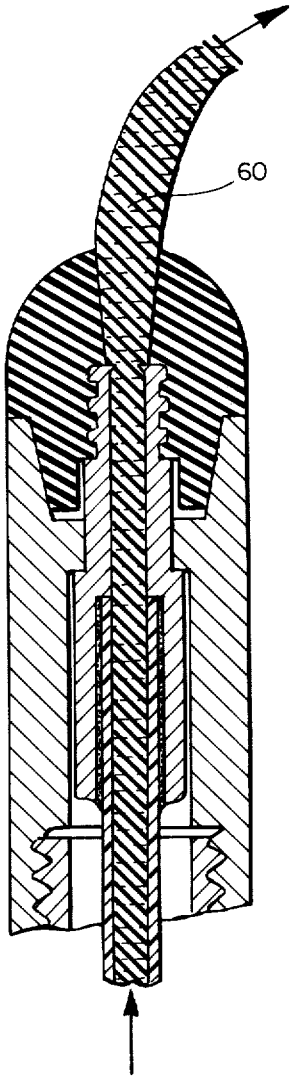
FIG. 4 is an illustration in cross-section of the terminal end of the apparatus of FIG. 3 shown with fluid uncured elastomeric material shown in the internal feed tube.

The apparatus 20 shown in FIG. 1 is specifically designed for use in the method of this invention. The apparatus 20 includes a tubular extension 22, a dispensing apparatus 24, and a control handle 26 for both operating the dispensing means and positioning the tip 10 on the end of the tubular extension 22.

The tubular extension 22 has a rigid section which is adjacent to the control handle 26. The opposite terminal end portion 28 on which the tip 10 is secured is flexible. One end of each control wire 30, 32 is attached to the end portion of the flexible section 28. The control wires 30, 32 are connected at their opposite ends to a pair of separately controlled drums 34 (only one drum is shown) mounted on the control [hand] *handle* 26. By adjustment of the drums 34 to either to collect or release the wires 30, 32 the position of the tip 10 can be adjusted and bent in a curved configuration shown in FIG. 2.

At the flexible terminal end 28 a metal connector 36 is provided which has annular piston [ring] *rings* 38 which [mates] *mate* with the piston rings 16 on the tip 10. The metal connector 36 further has defined in it a constricted area having a sharp cut off portion 40.

A tube 42 extends from the dispensing means 24, through the tubular extension 22 to the aperture 14 in the tip 10.

The dispensing means 24 consists of a mixing syringe 44 in which the plunger 46 is adapted to provide mixing of a fluid elastermeric material, a catalyst and other additive as may be required. The syringe 44 is mounted on top of the control handle 26 with the plunger 46 in contact with a rack 48 and a pivotal mounted pawl 50. The pawl 50 is connected to a trigger 52. Squeezing the trigger 52 causes the plunger 46 to be advanced within the syringe [46] *44* and material within the syringe 44 to be dispensed through the tube 42 to the tip 10.

In the method of this invention the tip 10 is inserted over the end of the flexible portion 28 of the tubular extension. The tip 10 being premolded of a silicone rubber is somewhat elastic and deforms somewhat until the piston ring 16 of the tip of 10 engages and locks with the mating piston rings 38.

The tubular extension [20] *22* with tip 10 installed is inserted into the vagina 54, through the cervical os 56 into the uterine cavity 58. Then, preferably using [flouroscopic] *fluoroscopic* techniques, the tip 10 is aligned with the uterine end of one of the oviducts 12. It should be noted that because of the shape of the uterine cavity 58 the tip can be guided blindly in the proper position. The relative position of the flexible end 28 is controlled by adjustment of the drums 34.

Figure 5:
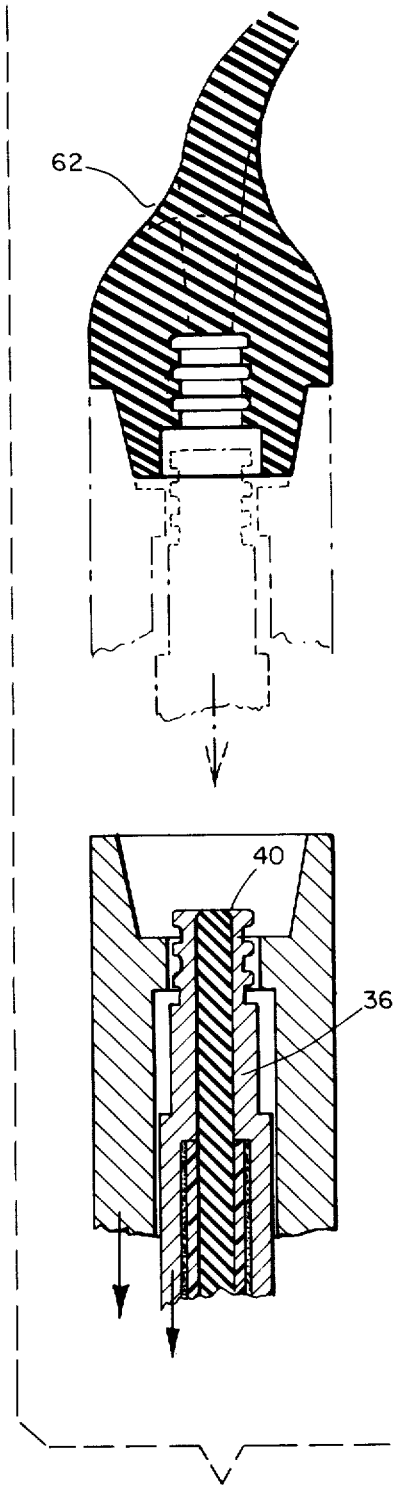
FIG. 5 is an illustration shown in cross-section showing the separation of the tip from the apparatus of FIG. 1.

Once the tip 10 is in position the fluid mixture of the elastomer, catalyst and other additives are injected through the tube 42 to the tip 10 by operation of the trigger 52 as noted above. The uncured fluid elastomeric mixture 60 flows through the aperture 14 in the tip 10 and then into the oviduct 12. A sufficient amount of the mixture is injected to fill approximately one third or more of the length of the oviduct 12. Some of the material will flow back around the tip 10 so that the surface of the tip 10 will conform to the shape of the uterine end of the oviduct 12 as shown in the tip 10 as modified 62 which is shown in FIG. 5.

The injected elastomeric material 60 is allowed to cure and solidify. The cured material will adhere to the tip 10 to make an essential single unit.

Once the elastomeric material has cured, the tube [40] *42* and the terminal end [36] *28* are withdrawn within the tubular extension 22. The edge 40 cuts the cured material which remains in the tube 42 from the cured material in the aperture 14 of the tip 10. Continued withdrawal of the terminal end [36] *28* results in the tip 10 being stripped from the terminal end as shown in phantom in FIG. 5.

The procedure noted above is repeated for the opposite oviduct to complete the sterilization procedure.

The solidified oviduct blocks each has a configuration which conforms to the interior of the oviduct in which it is cast, thus effectively preventing conception.

*The shaped tip member has an aperture defined therein and a configuration such as to fit in substantial sealing contact adjacent to the uterine end of the oviduct of the female. It has a size larger than the lumen of said oviduct and is positioned within the uterine cavity of said female adjacent to the uterine end of said oviduct with the aperture of said tip member being in axial alignment with the lumen of said oviduct, whereby the tip member remains within the uterine cavity where it can be gripped by mechanical means to remove the oviduct block nonsurgically.*

The oviduct block can remain in place until it is desired to remove it. The use of a material having approximately the same modulus of elasticity as the oviducts assists in maintaining the oviduct blocks 64 in position. The natural convolution of the oviduct likewise results in stabilization of the oviduct blocks 64. The tip 10 serves a most important function of preventing the oviduct block 64 from migrating into the intraperitoneal cavity, a problem that was a serious and relatively common problem with other similar prior art [technique] *techniques.*

As noted above the oviduct block is inserted nonsurgically. The method is relatively simple to learn by those skilled in the medical art. The time required is likewise quite short with a skilled person being able to block both oviducts in about 15 to 30 minutes.

As noted above the oviduct block can be removed nonsurgically if desired. An instrument of the type shown in FIG. 1 is used for this purpose. The tip 10 is replaced with a hooked member which is adapted to engage the loop 18. Once the loop 18 is engaged the oviduct block 64 is withdrawn. It is also possible to use a pronged member to grip the tip and then pull out the oviduct block.

Both the insertion and removal of the oviduct block 64 are relatively painless. However a local anesthetic can be used if desired.

The effectivenes of the contraception method of this invention was found to be excellent. On rabbit tests it was found that the method is 100% effective if the oviduct blocks are properly placed. In further rabbit tests it was found that after the oviduct blocks were removed that fertility was restored. There was no indication of expulsion of the oviduct blocks either in the uterine cavity or in the intraperitoneal cavity. Histologic examination and scanning election microscopic examination have not indicated that there is any adverse reaction to the tissue of the oviducts.

The apparatus of this invention has been described in *the* preferred embodiment. It should be appreciated that [the] various modifications can be made to the apparatus without departing from the scope of this invention. For example, the control handle 26 has been provided to enable a simple one handed operation of the apparatus. [If] *It* is possible, however, to simply use control wires which are operated by the fingers of the hand rather than the drums. Further, the dispensing apparatus consisting of the trigger 52, rack 48 and pawl 50, could likewise be removed and the syringe operated manually. Furthermore, the configuration of the tip 10 can be modified to a different shape such as a conical configuration [of] *or* other suitable shapes and still be satisfactory for use in this invention. These and other modifications which would be obvious to those skilled in the art are included within the scope of the subjoined claims.

I claim:

1. The method of forming non-surgically removable oviduct block in a female comprising the step of a. providing a shaped tip member having an aperture defined therein; said tip member having a configuration such as to fit in substantial sealing contact adjacent to the uterine end of the oviduct of said female, and having a size larger than the lumen of said oviduct; said tip member being formed from a given cured elastomeric material b. positioning said tip member within the uterine cavity of said female adjacent to the uterine end of said oviduct with the aperture of said tip member being in axial alignment with the lumen of said oviduct c. injecting through the aperture of said tip member into the lumen of said oviduct a mixture of a fluid self curing elastomeric material which will solidify in said oviduct and adhere to said tip member, said elastomeric material being injected into said oviduct in an amount sufficient to block the passage of ovum through said oviduct to the uterine cavity d. and thereafter allowing said uncured elastomeric material to cure to a solidified mass while in contact with said tip member, whereby an oviduct block is formed wherein the tip member remains within the uterine cavity where it can be gripped by mechanical means to remove the oviduct block non-surgically.

2. The method according to claim 1 wherein said tip member further includes a loop member whereby said loop member can be gripped to non-surgically remove said oviduct block.

3. The method according to claim 1 wherein said self-curing elastomeric material is a self-curing silicone elastomer.

4. The method according to claim 1 wherein said self-curing elastomeric material when solidified has a modulus of elasticity substantially the same as said oviduct.

5. The apparatus for forming the oviduct block according to claim 1, said apparatus comprising: a tubular means of a length sufficient to extend from vagina area of said female to the uterine ends of said oviducts and having a diameter sufficiently small to pass through the cervix of said female; said tubular means having first and second terminal ends; said first terminal end having an apertured tip member detachably connected thereto and also means for releaseably holding and ejecting said tip member, said tubular member including means for positioning said first terminal end with said tip member thereon adjacent the uterine end of said oviduct, and said tubular member further including means for transmission of said self curing elastomeric material from a point adjacent to the second terminal end to and through said aperture in said tip member secured to the first terminal end.

6. The apparatus of claim 5 in which the first terminal end portion is flexible.

7. The apparatus according to claim 5 in which the position of the first terminal end is controlled by means operable from the second terminal end.

8. The apparatus according to claim 5 wherein the means for holding and ejecting said tip member comprises a slideable member positioned within said tubular member whereby when a tip member is secured at the first terminal end to said slideable member and said slideable member is drawn through said tubular member toward the second terminal end said tip is removed from said slideable member.

9. The apparatus according to claim 5 wherein the dispensing means is a syringe having a barrel and a plunger and wherein the plunger is advanceable within the barrel by a rack and pawl drive operated from the second terminal end.

*10. Apparatus for forming an oviduct block comprising: a tubular means having a length sufficient to extend from the vagina area of a female to the uterine end of the oviduct and having a diameter sufficiently small to pass longitudinally through the cervix of said female; said tubular means having first and second terminal ends; said first terminal end having means to engage and connect a tip member thereto, said tubular means including means therein for adjustably displacing said first terminal end laterally relative to said second terminal end to position said first terminal end adjacent the uterine end of said oviduct to cause the tip member to at least temporarily block said uterine end; said tubular means further including fluid passage means for transmission of a plastic material from a point adjacent to the second terminal end into said oviduct beyond said tip member at first terminal end of said tubular means, and means to dispense a sufficient amount of said material to fill a predetermined length of the oviduct and to flow into engagement with the tip member at the uterine end of said oviduct, to form a block having an enlarged end portion exposed in the uterine end of the oviduct.*

*11. The apparatus of claim 10 in which the tubular means adjacent the first terminal end has a flexible portion separable from the block formed by said plastic material, said flexible portion affording displacement of said first terminal end relative to said second terminal end.*

*12. The apparatus according to claim 10 in which the adjustable means is operable from the second terminal end.*

*13. The apparatus according to claim 10 in which the means for dispensing said plastic material is a syringe having a barrel and a plunger, the plunger being advanceable within the barrel by a rack and pawl drive operated from the second terminal end to dispense said sufficient amount.*

*14. Apparatus for forming an oviduct block comprising: a tubular means having a length sufficient to extend from the vagina area of a female to the uterine end of the oviduct and having a diameter sufficiently small to pass through the cervix of said female; said tubular means having first and second terminal ends; said first terminal end including means for holding and releasing a tip member, said tubular means including means for positioning said first terminal end with said tip member thereon adjacent the uterine end of said oviduct to at least temporarily block said uterine end; said tubular means further including fluid passage means for transmission of a plastic material from a point adjacent to the second terminal end into said oviduct beyond said tip member at first terminal end of said tubular means, and means to dispense a sufficient amount of said material to fill a predetermined length of the oviduct and to flow into engagement with the tip member at the uterine end of said oviduct, to form a block having an enlarged end portion exposed in the uterine end of the oviduct, said holding and releasing means comprising a slidable member positioned within said tubular means, whereby when the tip member is held at the first terminal end by said slidable member and said slidable member is drawn through said tubular means toward the second terminal end, said tip member is released from said slidable member.*

*15. A non-surgically removable oviduct block for a female, comprising: a solid body of solidified plastic material having a transverse dimension conforming to the interior of the oviduct and having at one end a solid molded tip portion with a configuration adapted to fit in contact with the uterine end of the oviduct of said female forming a single unit; said molded tip portion having a transverse dimension larger than the interior of the oviduct to prevent said block from migrating into the intraperitoneal cavity, whereby said tip portion remains accessible from the uterine cavity, said molded tip portion having means thereon which can be gripped by mechanical means to remove the oviduct block non-surgically; said body of plastic material having a length providing a volume sufficient to block the passage of ovum through said oviduct to the uterine cavity of said female.*

*16. The oviduct block of claim 15 in which the plastic material forming the oviduct block has approximately the same modulus of elasticity as the oviduct.*

*17. The oviduct block of claim 15 in which the length of said plastic material body is at least one third of the length of the oviduct.*

*18. The oviduct block of claim 15 in which the plastic material is a cured elastomeric material.*

*19. The oviduct block of claim 18 in which the elastomeric material is a self-curing silicone elastomer.*

*20. The oviduct block of claim 15 in which the tip portion includes a loop member comprising said means to be gripped to non-surgically remove said oviduct block from the oviduct.*

*21. The method of forming non-surgically removable oviduct block in a female, comprising the steps of:*

*a. introducing an injecting means through the cervical os into the uterine cavity of said female;*

*b. providing a pre-formed tip member having an aperture therein adjacent to the uterine end of the oviduct of said female to limit the flow of material dispensed by the injecting means;*

*c. injecting from said injecting means through said aperture into the interior of said oviduct beyond said tip member a plastic material which will flow into engagement with said tip member, said plastic material being injected into said oviduct in an amount sufficient to block the passage of ovum through said oviduct to the uterine cavity; and*

*d. allowing said plastic material to solidify in said oviduct in contact with said tip member to provide a single-unit oviduct block at least partially formed by said solidified plastic material, said tip member providing a portion larger than the interior of the end of said oviduct exposed in the uterine cavity, whereby the*

*exposed portion of the block can be gripped by mechanical means to remove the oviduct block non-surgically.*

*22. The method of forming non-surgically removable oviduct block in a female, comprising the steps of:*

*a. introducing an injecting means through the cervical os into the uterine cavity of said female;*

*b. providing a seal between said injecting means and the wall of the uterus in the marginal area circumscribing the uterine end of the oviduct of said female to limit the flow into the cavity of material dispensed by the injecting means;*

*c. injecting from said injecting means into the interior of said oviduct beyond said seal a plastic material which will flow into engagement with said seal, said plastic material being injected into said oviduct in an amount sufficient to block the passage of ovum through said oviduct to the uterine cavity; and*

*d. allowing said plastic material to solidify in said oviduct and provide an oviduct block at least partially formed by said solidified plastic material and having a tip portion larger than the interior of the end of said oviduct exposed in the uterine cavity, whereby the exposed portion of the block can be gripped by mechanical means to remove the oviduct block non-surgically.*

*23. The method according to claim 22 wherein said seal is provided by a pre-formed molded tip member having an aperture therein and the plastic material injected into the interior of the oviduct is injected through the aperture of said tip member.*

*24. The method according to claim 22 further including the step of providing a loop member on the exposed portion in said uterine cavity to permit removal of said oviduct block by engaging the loop and extracting said block.*

*25. The method of claim 22 in which the plastic material injected into the oviduct has approximately the same modulus of elasticity as the oviduct.*

*26. The method of claim 22 in which the plastic material is a self-curing elastomeric material.*

*27. The method of claim 26 in which the elastomeric material fills at least one third of the length of the oviduct.*

*28. The method of forming non-surgically removable oviduct block in a female, comprising the steps of:*

*a. introducing an injecting means through the cervical os into the uterine cavity of said female;*

*b. positioning the injecting means adjacent the uterine end of the oviduct and providing a seal with the uterine wall in the marginal area circumscribing the interior of the oviduct limiting the flow into the uterine cavity of material dispensed by the injecting means;*

*c. injecting from said injecting means into the interior of said oviduct beyond said seal a plastic material which will flow into engagement with said seal, said plastic material being injected into said oviduct in an amount sufficient to block the passage of ovum through said oviduct to the uterine cavity; and*

*d. allowing said plastic material to solidify in said oviduct and provide an oviduct block at least partially formed by said solidified plastic material, whereby the block can be gripped by mechanical means to remove the oviduct block non-surgically.*

*29. The method of claim 28 including the step of providing a molded tip portion as an integral part of said block, said tip having means directed toward and located in the uterine cavity and of a shape to be gripped for removal of the block.*

* * * * *